(12) United States Patent
Jayaramareddy et al.

(10) Patent No.: US 11,096,945 B2
(45) Date of Patent: Aug. 24, 2021

(54) PHARMACEUTICAL COMPOSITIONS OF LINAGLIPTIN AND PROCESS FOR PREPARATION THEREOF

(71) Applicants: Venugopala Chokkasandra Jayaramareddy, Hyderabad (IN); Sreenivas Reddy, Hyderabad (IN); Chandrashekhar Shriram Kandi, Hyderabad (IN); Sivakumaran Meenakshisunderam, Hyderabad (IN)

(72) Inventors: Venugopala Chokkasandra Jayaramareddy, Hyderabad (IN); Sreenivas Reddy, Hyderabad (IN); Chandrashekhar Shriram Kandi, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days.

(21) Appl. No.: 15/960,441

(22) Filed: Apr. 23, 2018

(65) Prior Publication Data
US 2018/0250304 A1    Sep. 6, 2018

Related U.S. Application Data

(63) Continuation-in-part of application No. 14/674,652, filed on Mar. 31, 2015, now abandoned.

(51) Int. Cl.
*A61K 31/522*   (2006.01)
*A61K 9/51*    (2006.01)
*A61K 9/50*    (2006.01)
*A61K 9/20*    (2006.01)
*A61K 9/28*    (2006.01)

(52) U.S. Cl.
CPC .......... *A61K 31/522* (2013.01); *A61K 9/2009* (2013.01); *A61K 9/2018* (2013.01); *A61K 9/2027* (2013.01); *A61K 9/2054* (2013.01); *A61K 9/2059* (2013.01); *A61K 9/2077* (2013.01); *A61K 9/2826* (2013.01); *A61K 9/2866* (2013.01); *A61K 9/5047* (2013.01); *A61K 9/5089* (2013.01); *A61K 9/5123* (2013.01); *A61K 9/5138* (2013.01); *A61K 9/5161* (2013.01)

(58) Field of Classification Search
CPC .............. A61K 31/155; A61K 2300/00; A61K 31/522; A61K 9/2009; A61K 9/2013; A61K 9/2018; A61K 9/2054; A61K 9/2059; A61K 31/00
See application file for complete search history.

(56) References Cited

FOREIGN PATENT DOCUMENTS

WO    WO-2011138380 A1  *  11/2011  .............. A61P 43/00

* cited by examiner

*Primary Examiner* — Jean P Cornet
(74) *Attorney, Agent, or Firm* — Jay R Akhave; PatentScience LLC

(57) ABSTRACT

Pharmaceutical compositions comprising an antidiabetic agent as an active agent are provided. The present invention relates to pharmaceutical compositions comprising linagliptin or a pharmaceutically acceptable salt thereof as an active agent. The present invention also relates to process of preparation of pharmaceutical compositions comprising linagliptin or a pharmaceutically acceptable salt thereof. The present invention also relates to method of administering the compositions comprising linagliptin to a subject in need thereof.

1 Claim, No Drawings

PHARMACEUTICAL COMPOSITIONS OF LINAGLIPTIN AND PROCESS FOR PREPARATION THEREOF

CROSS REFERENCE TO RELATED APPLICATIONS

This application claims priority from an Indian Patent Application IN 1774/CHE/2014 filed on Apr. 2, 2014 and is a continuation-in-part of U.S. Ser. No. 14/674,652 filed on Mar. 31, 2015

FIELD OF THE INVENTION

The present invention relates to pharmaceutical compositions comprising an antidiabetic agent as an active agent or a pharmaceutically acceptable salt thereof. The present invention also relates to pharmaceutical compositions comprising linagliptin as an active agent or a pharmaceutically acceptable salt thereof. The present invention also relates to a process for preparation of pharmaceutical compositions comprising linagliptin or a pharmaceutically acceptable salt thereof. The present invention also relates to method of administering the compositions comprising linagliptin in a subject in need thereof.

BACKGROUND OF THE INVENTION

Diabetes mellitus, or simply diabetes, is a group of metabolic diseases in which a person has high blood sugar, either because the pancreas does not produce enough insulin, or because cells do not respond to the insulin that is produced. This high blood sugar produces the classical symptoms of polyuria (frequent urination), polydipsia (increased thirst), and polyphagia (increased hunger). There are three main types of diabetes mellitus (DM):
   Type 1 diabetes mellitus or "insulin-dependent diabetes mellitus (IDDM)" or "juvenile diabetes" is characterized by loss of the insulin-producing beta cells of the islets of Langerhans in the pancreas, leading to insulin deficiency.
   Type 2 diabetes mellitus or "non insulin-dependent diabetes mellitus (NIDDM)" or "adult-onset diabetes" is characterized by insulin resistance, which may be combined with relatively reduced insulin secretion. The defective responsiveness of body tissues to insulin is believed to involve the insulin receptor. However, the specific defects are not known.
   Gestational diabetes, occurs when pregnant women without a previous diagnosis of diabetes develop a high blood glucose level. It may precede development of type 2 diabetes mellitus.

Insulin-dependent Diabetes mellitus (IDDM) is currently treated through the administration of insulin (isolated bovine or procine pancreases or produced as a recombinant molecule) to patients using different forms of administration. Non-insulin-dependent Diabetes mellitus (NIDDM) is treated by diet, administration of sulphonylureas to stimulate insulin secretion or with biguanides to increase glucose uptake. Resistant individuals may need insulin therapy. Traditional, as well as more modern, methods for the treatment of IDDM are characterized by a great deal of effort on behalf of the patient, high costs, and usually a drastic reduction in the quality of living of the patient. Standard therapy (daily i.v. injection of insulin), which has been used since the thirties, is directed at treating the acute symptoms but results, after prolonged application, in vascular disease and nerve damage [LACY, P., *Status of Islet Cell Transplantation. Diabetes Care* 16 (3) 76 (1993)].

Insulin-dependent Diabetes mellitus and Non-Insulin-dependent Diabetes mellitus can be treated by using of dipeptidylpeptidase IV inhibitor. Dipeptidylpeptidase 4 inhibitor, also DPP-4 inhibitors or gliptins, are a class of oral hypoglycemics and can be used to treat diabetes mellitus type 2. Glucagon increases blood glucose levels, and DPP-4 inhibitors reduce glucagon and blood glucose levels. The mechanism of DPP-4 inhibitors is to increase incretin levels (GLP-1 and GIP), which inhibit glucagon release, which in turn increases insulin secretion, decreases gastric emptying, and decreases blood glucose levels. It is observed that compounds which inhibit DPP-4 are correlatively, able to improve glucose tolerance, though not necessarily through mechanisms involving DPP-4.

Linagliptin is a Dipeptidyl peptidase 4 inhibitor belonging to the chemical class of quinazolin derivative and is approved for the treatment to improve glycemic control with type 2 diabetes mellitus. Glucagon-like peptide-1 (GLP-1) is an incretin hormone. When blood glucose levels are elevated, GLP-1 stimulates insulin secretion, decreases glucagon secretion, improves beta-cell function, and slows gastric emptying. GLP-1 production is reduced in patients with type 2 diabetes. Furthermore, once GLP-1 is produced, it is rapidly degraded by the Dipeptidyl peptidase-4 (DPP-4) enzyme. Hence, Linagliptin which is a Dipeptidyl peptidase-4 inhibitor is used.

The chemical name of Linagliptin is 1H-Purine-2,6-dione, 8-[(3R)-3-amino-1-piperidinyl]-7-(2-butyn-1-yl)-3,7-dihydro-3-methyl-1-[(4-methyl-2quinazolinyl)methyl]. Its molecular formula is $C_{25}H_{28}N_8O_2$ and the molecular weight is 472.54 g/mol. The chemical structure is:

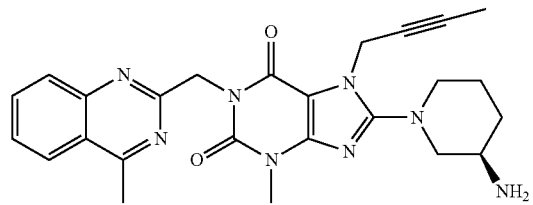 [SMILES: CC#CCn1c(N2CCC[C@@H](N)C2)nc2c1c(=O)n(Cc1nc(C)c3ccccc3n1)c(=O)n2C]

Linagliptin was approved on May 2, 2011 in USA and is currently marketed as Tradjenta® tablets and indicated as an adjunct to diet and exercise to improve glycemic control in adults with type 2 diabetes mellitus. The tablet formulation contains 5 mg of Linagliptin and the following ingredients: mannitol, pregelatinized starch, corn starch, copovidone, and magnesium stearate. Additionally, the film coating contains hypromellose, titanium dioxide, talc, polyethylene glycol, and red ferric oxide.

U.S. Pat. No. 7,407,955 discloses the compound Linagliptin. U.S. Pat. No. 8,178,541 discloses a pharmaceutical composition comprising a first compound Linagliptin or an enantiomer, mixture thereof, or a salt thereof; and one or more other therapeutic agents selected from antidiabetics, lipid lowering agents, active substances for the treatment of obesity, and drugs for treating high blood pressure; optionally together with one or more inert carriers and/or diluents.

US patent publication 2013/0122089 A1 discloses a pharmaceutical composition comprising as an active ingredient a DPP IV inhibitor compound (linagliptin) in an amount of 0.5 mg, 1 mg, 2.5 mg, 5 mg or 10 mg, or a salt thereof, a first diluent, a second diluent, a binder, a disintegrant and a lubricant, wherein the first diluent is mannitol, the second diluent is pregelatinized starch, the binder is copovidone, the disintegrant is corn starch, and the lubricant is magnesium stearate; and wherein the DPP IV inhibitor compound is present in an amount 0.5-20% based on the total weight of DPP IV inhibitor compound, first diluent, second diluent, binder, disintegrant and lubricant.

US patent publication 2013/0224296 A1 discloses a coated tablet comprising: (a) a tablet core wherein the tablet core comprises (i) optionally at least one antidiabetic agent or a pharmaceutically acceptable salt thereof, wherein the antidiabetic agent is other than saxagliptin; (b) a first layer that coats the tablet core, wherein the first layer comprises (i) a coating material; and (ii) optionally at least one water soluble antioxidant; (c) a second layer that coats the first layer wherein the second layer comprises (i) a coating material; (ii) at least one water soluble antioxidant; and (iii) an active pharmaceutical ingredient or a pharmaceutically acceptable salt thereof, wherein the active pharmaceutical ingredient is a primary amine or a secondary amine; and (d) a third layer that coats the second layer wherein the third layer comprises (i) a coating material; and (ii) optionally at least one water soluble antioxidant.

US patent publication 2013/0064887 A1 discloses a pharmaceutical composition comprising a) an inner extended release core comprising metformin or metformin hydrochloride and one or more excipients; b) an optional intermediate seal coating; and c) an outer immediate release coating comprising at least one active pharmaceutical ingredient selected from a DPP-4 inhibitor and a SGLT-2 inhibitor, and one or more excipients.

US patent publication 2011/0206766 A1 discloses a composition comprising a DPP-4 inhibitor and a partner drug and a basic agent for stabilizing said DPP-4 inhibitor against degradation.

US patent publication 2010/0209506 A1 discloses a pharmaceutical composition comprising Linagliptin or a pharmaceutically acceptable salt thereof as a first active pharmaceutical ingredient with combination of 1-chloro-4-(β-D-glucopyranos-1-yl)-2-[4-((S)-tetrahydrofuran-3-yloxy)-benzyl]-benzene as a second active pharmaceutical ingredient, one or more diluents, one or more binders and one or more disintegrants.

US patent publication 2012/0296091 A1 discloses anhydrous polymorph A and B of Linagliptin. US patent publication 2013/0123282 A1 discloses crystalline form X of linagliptin with characteristic XRD pattern.

PCT publication WO 2013/128379 A2 discloses Form I of Linagliptin respectively characterized by X-ray powder diffraction. The said PCT publication WO '379 also discloses crystalline Linagliptin Form I wherein 90% of particles have particle size less than 300 μm.

PCT publication WO 2012/152837 A1 discloses crystalline form of Linagliptin benzoate having an X-ray powder diffraction pattern comprising peaks at 2-theta angles of 8.0±0.2°, 8.7±0.2°, 10.4±0.2°, 12.9±0.2°, 13.8±0.2° and 17.4±0.2°. PCT publication WO 2014/080384 A1 claims compositions of linagliptin which is devoid of mannitol. Further, the said publication discloses mannitol at 90% w/w of the composition.

IN patent publication 653/MUM/2012 discloses a storage stable amorphous form of Linagliptin substantially free from residual organic solvents. The said IN patent publication '653 further discloses amorphous form of Linagliptin of particle size of $D_{10}$ less than about 50 μm, $D_{50}$ less that about 200 μm, $D_{90}$ less than about 400 μm, and $D_{95}$ less than about 100 microns.

U.S. Pat. No. 9,867,829 discloses a coated pharmaceutical composition comprising: a composition comprising linagliptin or a pharmaceutically acceptable salt thereof as active ingredient; mannitol; copovidone; and magnesium stearate, wherein the mannitol is present in an amount greater than 90 to 95% by weight, based on the weight of the pharmaceutical composition; and a coating comprising hydroxypropylmethylcellulose on the composition. The main aim of the said U.S. Pat. No. 9,867,829 is to provide a pharmaceutical composition which is stable and shows a favorable dissolution profile after storage under humid conditions. However, one of the difficulties experienced with high amounts of mannitol (90 to about 95% w/w) in pharmaceutical formulations is that it hinders the free flow of the blend composition which leads to improper/non-consistent filling of blend into the dies of a tablet press during the tablet compression, this ultimately leads to Tablet defects i.e. Sticking & Picking during Tablet compression. Also these Linagliptin Tablets, especially with high amounts of mannitol, for eg. 93% of mannitol found to have very low drug dissolution rate, especially up to 30 minutes, which is unacceptable for immediate release dosage forms.

SUMMARY OF THE INVENTION

An aspect of the present invention provides pharmaceutical compositions comprising therapeutically effective amount of a Dipeptidyl peptidase-4 inhibitor as an active agent(s), at least one diluent, and optionally one or more other pharmaceutically acceptable excipient(s).

Another aspect of the present invention provides pharmaceutical compositions comprising linagliptin as an active agent(s), at least one diluent in an amount of from about 0.1% w/w to about 99.0% w/w of the total weight of the composition, and optionally one or more other pharmaceutically acceptable excipient(s).

In an aspect the present invention provides pharmaceutical compositions comprising linagliptin as an active agent(s), at least one diluent other than a sugar alcohol in an amount of from about 0.1% w/w to about 99.0% w/w of the total weight of the composition, and optionally one or more other pharmaceutically acceptable excipient(s).

In another aspect the present invention provides pharmaceutical compositions comprising linagliptin as an active agent(s), at least one diluent other than pregelatinised starch in an amount of from about 0.1% w/w to about 99.0%/0 w/w of the total weight of the composition, and optionally one or more other pharmaceutically acceptable excipient(s).

Yet another aspect of the present invention provides pharmaceutical compositions comprising linagliptin as an active agent(s), a first diluent other than sugar alcohol and a second diluent other than pregelatinised starch in an amount of from about 0.1% w/w to about 99.0% w/w of the total weight of the composition, and optionally one or more other pharmaceutically acceptable excipient(s).

An aspect of the present invention provides pharmaceutical compositions comprising linagliptin as an active agent(s), at least one diluent other than pregelatinised starch in an amount about 85.0% w/w of the total weight of the composition, at least one binder, at least one disintegrant and optionally one or more other pharmaceutically acceptable excipient(s). In another aspect, the present invention provides pharmaceutical compositions comprising linagliptin as an active agent(s), at least one diluent other than pregelatinised starch, which is mannitol in an amount of about 85.0% w/w of the total weight of the composition, at least one binder which is copovidone in an amount less than about 3.0% w/w of the total weight of the composition, at least one disintegrant which is corn starch in an amount less than about 2.0%/0 w/w of the total weight of the composition and optionally one or more other pharmaceutically acceptable excipient(s).

An aspect of the present invention provides pharmaceutical compositions comprising linagliptin as an active agent in an amount less than 5.0%/0 w/w of the total weight of the composition, mannitol in an amount between 80.0 w/w to 90.0% w/w of the total weight of the composition, at least one binder and at least one disintegrant and optionally other pharmaceutically acceptable excipients present in the composition, with the proviso that the composition is free of pregelatinised starch. An aspect of the present invention provides pharmaceutical compositions comprising linagliptin as a sole active agent in an amount less than 5.0% w/w of the total weight of the composition, mannitol in an amount between 80.0 w/w to 90.0% w/w of the total weight of the composition, at least one binder and at least one disintegrant and optionally other pharmaceutically acceptable excipients present in the composition, with the proviso that the composition is free of pregelatinised starch.

In another aspect the present invention provides pharmaceutical compositions comprising linagliptin in an amount less than 5.0% w/w of the total weight of the composition, mannitol in an amount between 80.0% w/w to 90.0% w/w of the total weight of the composition, copovidone in an amount less than 3.0% w/w of the total weight of the composition, corn starch in an amount less than 2.0% w/w of the total weight of the composition and optionally one or more other pharmaceutically acceptable excipients(s).

Yet another aspect the present invention provides pharmaceutical compositions comprising linagliptin in an amount less than 5.0% w/w of the total weight of the composition, mannitol in an amount about 84.0% w/w of the total weight of the composition, copovidone in an amount less than 3.0% w/w of the total weight of the composition, corn starch in an amount less than 2.0% w/w of the total weight of the composition and a coating comprising hydroxypropylmethylcellulose on the composition.

In an aspect, the present invention provides process for the preparation of pharmaceutical compositions of linagliptin, wherein the process comprises of the following steps:
  i) treating linagliptin with at least one diluent,
  ii) optionally adding one or more other pharmaceutically acceptable excipients, and,
  iii) formulating into a suitable dosage form.

In another aspect, the present invention provides process for the preparation of pharmaceutical compositions of linagliptin, wherein the process comprises of the following steps:
  i) treating linagliptin with mannitol,
  ii) optionally adding one or more other pharmaceutically acceptable excipients,
  iii) formulating into a suitable dosage form, and,
  iv) coating the dosage form.

In an aspect, the present invention provides a process for the preparation of pharmaceutical composition of linagliptin, wherein the process comprises of the following steps:
  i) treating linagliptin with at least one diluent,
  ii) optionally adding a second active agent(s),
  iii) optionally adding one or more other pharmaceutically acceptable excipients, and,
  iv) formulating into a suitable dosage form.

In another aspect, the present invention provides process for the preparation of pharmaceutical compositions of linagliptin, wherein the process comprises of the following steps:
  i) treating linagliptin with mannitol,
  ii) optionally adding a second active agent(s),
  iii) optionally adding one or more other pharmaceutically acceptable excipients,
  iv) formulating into a suitable dosage form, and,
  v) coating the dosage form.

An aspect of the present invention relates to the method of using such compositions for inhibiting the activity of the enzyme dipeptidylpeptidase-IV (DPP-IV) and for the prevention or treatment of diseases or conditions associated with an increased DPP-IV activity, or diseases or conditions capable of being prevented or alleviated by reducing the DPP-IV activity. The compositions of the present invention are particularly useful in the prevention or treatment of type II diabetes mellitus.

DETAILED DESCRIPTION OF THE INVENTION

The term "particle size" unless indicated otherwise in the specification relates to particles of Linagliptin free base as well as pharmaceutically acceptable salt, amorphous or crystalline, anhydrous, esters, or isomer or derivative, hydrate, prodrug or solvates thereof. Linagliptin with specific "particle size" and distribution or surface area would provide a faster dissolution of the active ingredient. The compositions of the present invention are easy to prepare and are highly stable, and exhibit faster solubility and desired bioavailability. Particularly, according to an embodiment of the present invention, Linagliptin having an average particle size less than 200 microns, and/or surface area less than about 5 $m^2/gm$ are useful in making the compositions according to the present invention.

The term "therapeutically effective amount" is defined to mean the amount or quantity of the active drug (linagliptin), which is sufficient to elicit an appreciable biological response when administered to the patient.

In accordance with the present invention, the term "linagliptin" unless indicated otherwise in the entire specification, refers to linagliptin in the form of free base or its pharmaceutically acceptable salt, amorphous, crystalline or any isomer or derivative, hydrate or solvate, prodrug or combinations thereof. Preferably linagliptin is in the form of free base.

The term "excipient" means a pharmacologically inactive component such as a diluent, disintegrant, carrier, or the like. The excipients that are useful in preparing a pharmaceutical composition are generally safe, non-toxic and are acceptable for veterinary as well as human pharmaceutical use. Reference to an excipient includes both one and more than one such excipient.

The phrase "medicinal package" unless indicated otherwise in the entire specification refers to bottle or blister pack or pouch or any corresponding packing known to a person skilled in the art in which the dosage form or the medicinal preparation is packed with or without a desiccant.

The term "desiccant" unless indicated otherwise in the entire specification refers to a substance used to remove/suppress/decrease the odor/smell or to absorb moisture which prevents degradation/decomposition of the active agent(s). The desiccant may be placed in the internal space of the medicinal package, irrespective of any particular limit, so long as the amount is sufficient to remove the odorous material, that is, sufficient to suppress or reduce the smell. The amount of the desiccant can vary depending on kind or shape of the desiccant, distance from the medicinal preparation capable of giving out smells, amount of the compound giving out smells, type of formulation, volume of the space where the medicinal preparation and the desiccant are placed, amount of the existing or produced odorous material, preservation condition of the medicinal package.

The phrase "substantially pure polymorphic form of linagliptin", unless otherwise specified is to be understood as a substance free of other polymorphic and/or pseudopolymorphic forms at amounts detectable with typical analytical methods such as X-ray powder diffraction and/or solid state infrared absorption, i.e. containing less than 10% of other polymorphic and/or pseudopolymorphic forms. The phrase "substantially pure form of linagliptin", unless otherwise specified is to be understood as a substance characterized by a content less than 1.5% of each of the related substances, and less than 0.5% of each of the known or unknown impurities.

As used in this specification, the singular forms "a", "an", and "the" include plural references unless the context clearly dictates otherwise. Thus, for example, a reference to "a process" includes one or more process, and/or steps of the type described herein and/or which will become apparent to those persons skilled in the art upon reading this disclosure and so forth.

The phrase "substantially pure polymorphic form of linagliptin", unless otherwise specified is to be understood as a substance free of other polymorphic and/or pseudopolymorphic forms at amounts detectable with typical analytical methods such as X-ray powder diffraction and/or solid state infrared absorption, i.e. containing less than about 10% of other polymorphic and/or pseudopolymorphic forms.

"Pharmaceutically acceptable excipient(s)" are components that are added to the pharmaceutical formulation other than the active ingredient linagliptin. Excipients may be added to facilitate manufacture, enhance stability, enhance product characteristics, enhance bioavailability, enhance patient acceptability, etc. Pharmaceutically acceptable excipient(s) used in the present invention are selected from but not limited to one or more of diluents, binders, disintegrants, lubricants, glidants, compression aids, colors, sweeteners, preservatives, surfactants, suspending agents, dispersing agents, film formers, flavors, printing inks, and any other excipient known to the art for making pharmaceutical formulations. It will be appreciated by the person skilled in the art that a particular excipient may perform multiple roles in the pharmaceutical composition, such as for example, it can act as both a binder and filler, or as a binder and filler and disintegrant.

Diluents increase the bulk of the composition. Diluents according to the present invention are selected from, but not limited to, sugars such as lactose, sucrose, dextrose, mannose, fructose, galactose; sugar alcohols such as sorbitol, mannitol, erythritol, xylitol, lactitol; organic acids such as malic acid, citric acid, tartaric acid, fumaric acid and the like; inorganic acids such as dibasic calcium phosphate, tribasic calcium phosphate, calcium carbonate, magnesium carbonate, magnesium oxide, and the like; starlac, starch, modified starches, maltodextrin, calcium sulfate, powdered cellulose, microcrystalline cellulose, silicified microcrystalline cellulose, magnesium alumino metasilicate and the like used either alone or in combinations thereof.

Binders hold the ingredients in the composition together. Exemplary binders are selected from, but not limited to group comprising cellulose or its derivatives including ethyl cellulose, hydroxypropyl cellulose, hydroxypropyl methylcellulose, methylcellulose and hydroxyethyl cellulose, carboxymethyl cellulose; gelatin, liquid glucose; starch and its derivatives (e.g. corn starch, maize starch, potato starch, pregelatinised starch); hydrocolloids; sugars; polyvinyl pyrrolidone, copovidone, sodium alginate, acacia, alginic acid, tragacanth, xanthan, acacia, and the like used either alone or combination thereof. The binder may be used in the range of about 1-20% w/w of the composition.

Disintegrants according to the present invention are selected from but not limited to group comprising, cellulose and its derivatives including low-substituted hydroxypropyl cellulose, cross-linked polyvinylpyrrolidone, sodium carboxymethylcellulose, cross-linked sodium carboxymethylcellulose, microcrystalline cellulose, sodium starch glycolate, ion-exchange resins, starch and modified starches including pregelatinized starch, formalin-casein, and the like used either alone or in combinations comprising one or more of the foregoing disintegrants. In an embodiment, the disintegrant may be used in the range of about 0.5-30% by weight of the composition.

Lubricants and glidants aid in the processing of powder materials. Exemplary lubricants are selected from but not limited to group comprising glycerol behenate, mineral oil, polyethylene glycol, sodium stearyl fumarate, magnesium stearate, calcium stearate, zinc stearate, stearic acid, talc, vegetable oil, and the like used either alone or in combinations comprising one or more of the foregoing lubricants. Exemplary glidants include but not limited to talc, silicon dioxide, cornstarch, and the like used either alone or in combination thereof.

Surfactants are compounds which are capable of improving the wetting of the drug and/or enhancing the dissolution. The surfactants can be selected from hydrophilic surfactants or lipophilic surfactants or mixtures thereof. The surfactants can be anionic, nonionic, cationic, and zwitterionic surfactants. Surfactants according to the present invention are selected from but not limited to group comprising polyoxyethylene alkyl aryl ethers such as polyoxyethylene lauryl ether, polyoxyethylene cetyl ether, polyoxyethylene stearyl ether, polyethylene glycol (PEG) fatty acid esters such as PEG monolaurate, PEG dilaurate, PEG distearate, PEG dioleate; polyoxyethylene sorbitan fatty acid ester such as polysorbate 40, polysorbate 60, polysorbate 80; sorbitan fatty acid mono esters such as sorbitan monolaurate, sorbitan monooleate, sorbitan sesquioleate, sorbitan trioleate, polyoxyethylene castor oil derivates such as polyoxyl castor oil, polyoxyl hydrogenated castor oil, sodium lauryl sulphate and the like used either alone or in combination thereof.

"Suitable solvent" according to the present invention can be any solvent in which the binder is soluble or dispersible and is selected from isopropyl alcohol, ethanol, water, acetone, methylene chloride and the like or mixtures thereof.

The term "composition" or "formulation" or "dosage form" or "medicinal preparation" as used herein synonymously include solid dosage forms such as granules, multi-unit particulate systems (MUPS), pellets, spheres, tablets, capsules, mini-tablets, layered tablets (e.g. bilayer or trilayer), inlaid tablets, tablet in tablet, beads, particles, pellets presented in a sachet, capsule or tablet capsules such as soft and hard gelatin; lozenges or sachets; granulates, microparticles, multiparticulates, powder and the like, and liquid dosage forms such as solutions, suspensions, emulsions, colloids and the like, meant for oral administration. The tablets in accordance with the present invention can be prepared by either direct compression, dry compression (slugging), or by wet granulation. The wet granulation method may comprise use of aqueous solvent such as water or an organic solvent such as ethanol, or a mixture thereof as the granulating aid.

The present invention provides pharmaceutical compositions comprising therapeutically effective amount of a Dipeptidyl peptidase-4 inhibitor as an active agent(s), at least one diluent, and optionally one or more other pharmaceutically acceptable excipient(s).

In an embodiment, the present invention provides pharmaceutical compositions comprising linagliptin or a pharmaceutically acceptable salt thereof as an active agent(s), at least one diluent in an amount of from about 0.1% w/w to 99.0% w/w of the total weight of the composition, and optionally one or more other pharmaceutically acceptable excipient(s).

In another embodiment, the present invention provides pharmaceutical compositions comprising linagliptin as an active agent(s), at least one diluent other than a sugar alcohol in an amount of from about 0.1% w/w to about 99.0% w/w of the total weight of the composition, and optionally one or more other pharmaceutically acceptable excipient(s).

In another embodiment, the present invention provides pharmaceutical compositions comprising linagliptin as an active agent(s), at least one diluent other than pregelatinised starch in an amount of from about 0.1% w/w to about 99.0% w/w of the total weight of the composition, and optionally one or more other pharmaceutically acceptable excipient(s).

In another embodiment, the present invention provides pharmaceutical compositions comprising linagliptin as an active agent(s), a first diluent other than sugar alcohol and a second diluent other than pregelatinised starch in an amount of from about 0.1% w/w to about 99.0% w/w of the total weight of the composition, and optionally one or more other pharmaceutically acceptable excipient(s).

In an embodiment, the present invention provides pharmaceutical compositions comprising linagliptin as an active agent(s), a first diluent which is mannitol in an amount less than about 40% w/w of the total weight of the composition, a second diluent which is pregelatinised starch in an amount less than about 3% w/w and more than about 40% w/w of the total weight of the composition and optionally one or more other pharmaceutically acceptable excipient(s).

In another embodiment, the present invention provides pharmaceutical compositions comprising linagliptin as an active agent(s), a first diluent which is mannitol in an amount more than about 88% w/w of the total weight of the composition, a second diluent which is pregelatinised starch in an amount less than about 3% w/w and more than about 40% w/w of the total weight of the composition and optionally one or more other pharmaceutically acceptable excipient(s).

In yet another embodiment, the present invention provides pharmaceutical compositions comprising linagliptin as an active agent(s), at least one diluent other than pregelatinised starch in an amount more than about 85.0% w/w of the total weight of the composition, at least one binder, at least one disintegrant and optionally one or more other pharmaceutically acceptable excipient(s).

In another embodiment, the present invention provides pharmaceutical compositions comprising linagliptin as an active agent(s), at least one diluent other than pregelatinised starch which is mannitol in an amount more than about 85.0% w/w of the total weight of the composition, at least one binder which is copovidone in an amount less than about 3.0% w/w of the total weight of the composition, at least one disintegrant which is corn starch in an amount less than about 2.0% w/w of the total weight of the composition and optionally one or more other pharmaceutically acceptable excipient(s).

In an embodiment, the present invention provides pharmaceutical compositions comprising linagliptin as an active agent in an amount less than 5.0% w/w of the total weight of the composition, mannitol in an amount between 80.0 w/w to 90.0% w/w of the total weight of the composition, at least one binder and at least one disintegrant and optionally other pharmaceutically acceptable excipients present in the composition, with the proviso that the composition is free of pregelatinised starch.

In an embodiment, the present invention provides pharmaceutical compositions comprising linagliptin as a sole active agent in an amount less than 5.0% w/w of the total weight of the composition, mannitol in an amount between 80.0 w/w to 90.0% w/w of the total weight of the composition, at least one binder and at least one disintegrant and optionally other pharmaceutically acceptable excipients present in the composition, with the proviso that the composition is free of pregelatinised starch.

In another embodiment, the present invention provides pharmaceutical compositions comprising linagliptin in an amount less than 5.0% w/w of the total weight of the composition, mannitol in an amount between 80.0% w/w to 90.0% w/w of the total weight of the composition, copovidone in an amount less than 3.0% w/w of the total weight of the composition, corn starch in an amount less than 2.0% w/w of the total weight of the composition and optionally one or more other pharmaceutically acceptable excipients (s).

In yet another embodiment, the present invention provides pharmaceutical compositions comprising linagliptin in an amount less than 5.0% w/w of the total weight of the composition, mannitol in an amount about 84.0% w/w of the total weight of the composition, copovidone in an amount less than 3.0% w/w of the total weight of the composition, corn starch in an amount less than 2.0% w/w of the total weight of the composition and a coating comprising hydroxypropylmethylcellulose on the composition.

In another embodiment, the present invention provides pharmaceutical compositions comprising linagliptin as a first active agent(s), optionally a second active agent(s), at least one diluent and optionally one or more other pharmaceutically acceptable excipient(s).

In an embodiment, the second active agent(s) is selected from but not limited to group comprising pioglitazone hydrochloride, troglitazone, rosiglitazone; alpha-glucosidase inhibitors (e.g., voglibose, acarbose, miglitol, emiglitate etc.); biguanides (e.g., phenformin, metformin, buformin etc.); sulfonylureas (e.g., tolbutamide, glibenclamide, gliclazide, chlorpropamide, tolazamide, acetohexamide, glyclopyramide, glimepiride, glipizide, glybuzole etc.); repaglinide, senaglinide, nateglinide, mitiglinide or its calcium salt hydrate; amyrin agonists (e.g., pramlintide etc.), phosphotyrosine phosphatase inhibitors (e.g., vanadic acid etc.), dipeptidylpeptidase IV inhibitors; beta.3 agonists; gluconeogenesis inhibitors (e.g., glycogen phosphorylase inhibitor, glucose-6-phosphatase inhibitor, glucagon antagonist etc.), SGLT (sodium-glucose cotransporter) inhibitors (e.g., T-1095 etc.) and the like, and mixtures thereof.

In one of the embodiments, linagliptin exists in substantially pure crystalline forms A, B, C, D or E or in the form of mixture of two or more of the said polymorphic forms in the composition of the present invention, as disclosed in US patent publication 2012/0296091 A1 incorporated herein by reference. In another embodiment, linagliptin exists in amorphous form.

In an embodiment of the present invention, the composition comprises Linagliptin along with one or more pharmaceutically acceptable excipients, wherein the said composition contains more than about 3% w/w of polymorphic form A based on the total weight of the composition.

In an embodiment of the present invention, the composition comprises Linagliptin along with one or more pharmaceutically acceptable excipients, wherein the said composition contains more than about 3% w/w of polymorphic form B based on the total weight of the composition.

In an embodiment, the compositions of the present invention may additionally comprise of a colorant in order to produce a desirable color. Colors known to be 'FD&C' certified may be used to provide coloring to the product and are within the purview of the present invention. Suitable colorants include natural colorants i.e., pigments and dyes obtained from mineral, plant, and animal sources. Examples of natural colorants include red ferric oxide, yellow ferric oxide, annattenes, alizarin, indigo, rutin, quercetin, and the like. Synthetic colorants may also be used, which is typically an FD&C or D&C dye selected from the so-called 'coal-tar' dyes, such as a nitroso dye, a nitro dye, an azo dye, an oxazine, a thiazine, a pyrazolone, a xanthene, an indigoid, an anthraquinone, an acridine, a rosaniline, a phthalein, a quinoline, or a 'lake' thereof, i.e. an aluminum or calcium salt thereof. Particularly preferred colorants are food colorants in the 'GRAS' (Generally Regarded as Safe) category.

In an embodiment, the tablet compositions of the present invention may be film coated. A film forming agent may provide smooth film-forming coating suspensions and enhance the rheological mechanical strength properties of film coating gel matrices. Film forming agents include, for example, polyvinylpyrrolidone, natural gums, starches, and cellulosic polymers. A cellulosic polymer may include a molecule comprising at least one cellulose polymer or derivative modified with small amounts of propylene glycol ether groups attached to the cellulose anhydroglucose chain affording binding properties that enhance the reinforcing film properties of film applications. Examples of cellulosic polymers include, but are not limited to, hydroxypropyl methyl cellulose ("HPMC"), carboxymethyl cellulose ("CMC") or salts thereof, hydroxypropyl cellulose ("HPC"), methylcellulose ("MC"), hydroxyethyl cellulose ("HEC"), and the like. In addition, cellulosic polymers may be characterized as ionic or non-ionic. Ionic cellulosic polymers include, for example, sodium CMC. Non-ionic cellulosic polymers include, for example, HPMC, HPC, HEC, and MC. Varieties of commercially available cellulosic polymers exist and may include, for example, Spectracel® HPMC compositions (available from Sensient Technologies). Further, other commercially available coating materials are available marketed under the brand name Opadry® for example Opadry® II Gray which contains: lactose monohydrate NF, hypromellose type 2910 USP, titanium dioxide USP, triacetin USP, and iron oxide black JPE; Opadry® II Pink which contains: hypromellose type 2910 USP, titanium dioxide USP, lactose monohydrate NF, polyethylene glycol 3350 NF, triacetin USP, and FD&C Red #40; Opadry® II Blue which contains: hypromellose type 2910 USP, lactose monohydrate NF, FD&C Blue #1, polyethylene glycol 3350 NF, FD&C Blue #2, titanium dioxide USP, triacetin USP, and D&C Yellow #10; Opadry® II Yellow which contains: hypromellose type 2910 USP, lactose monohydrate NF, titanium dioxide USP, iron oxide yellow NF, polyethylene glycol 3350 NF, and triacetin USP; Opadry® II Purple which contains: hypromellose type 2910 USP, lactose monohydrate NF, titanium dioxide USP, D&C Red #27, polyethylene glycol 3350 NF, triacetin USP, and FD&C Blue #1 and the like. In an embodiment, the coating composition employed may be an aqueous, non-aqueous or a hydroalcoholic system. The solvents used to prepare a non-aqueous coating composition is selected from but not limited to a group comprising dehydrated alcohol, isopropyl alcohol, methylene chloride, acetone or any other solvent known to the art for such use, or mixtures thereof.

The compositions of the present invention are chemically stable against degradation by oxidation, hydrolysis, isomerisation, photolysis, polymerization, or any other method of degradation, either as a result of mixing with excipients or by any other method. Chemical stability can be measured by a suitable, stability indicating chromatographic method for determining degradation products (see Aulton Me., *Pharmaceutics—The Science of Dosage Form Design,* 2.sup.nd Edition, 2002, Churchill Livingstone).

The compositions of the present invention can be packed into suitable containers such as bottles, blisters or pouch. Further, the packages may optionally contain a desiccant or an antioxidant or oxygen absorbent or combinations thereof.

In an embodiment, the present invention provides a process for the preparation of pharmaceutical compositions of linagliptin, wherein the process comprises of the following steps:
  i) treating linagliptin with at least one diluent,
  ii) optionally adding one or more other pharmaceutically acceptable excipients, and,
  iii) formulating into a suitable dosage form.

In another embodiment, the present invention provides process for the preparation of pharmaceutical compositions of linagliptin, wherein the process comprises of the following steps:
  i) treating linagliptin with mannitol,
  ii) optionally adding one or more other pharmaceutically acceptable excipients,
  iii) formulating into a suitable dosage form, and,
  iv) coating the dosage form.

In an embodiment, the present invention provides the process for the preparation of pharmaceutical compositions of linagliptin, wherein the process comprises of the following steps:
  i) treating linagliptin with at least one diluent,
  ii) optionally adding a second active agent(s),
  iii) optionally adding one or more other pharmaceutically acceptable excipients, and,
  iv) formulating into a suitable dosage form.

In another embodiment, the present invention provides process for the preparation of pharmaceutical compositions of linagliptin, wherein the process comprises of the following steps:
  i) treating linagliptin with mannitol,
  ii) optionally adding a second active agent(s),
  iii) optionally adding one or more other pharmaceutically acceptable excipients,
  iv) formulating into a suitable dosage form, and,
  v) coating the dosage form.

Another embodiment of the present invention relates to the method of using such compositions for inhibiting the activity of the enzyme dipeptidylpeptidase-IV (DPP-IV) and for the prevention or treatment of diseases or conditions associated with an increased DPP-IV activity, or diseases or conditions capable of being prevented or alleviated by reducing the DPP-IV activity. The compositions of the present invention are particularly useful in the prevention or treatment of type II diabetes mellitus.

The following examples serve to illustrate the embodiments of the present invention. However, they do not intend to limit the scope of the invention. It is obvious to those skilled in the art to find out the composition for other dosage forms and substitute the equivalent excipients as described in this specification or with the one known to the industry.

Example 1

| S. No. | Ingredients | % w/w |
|---|---|---|
| | Intragranular Ingredients | |
| 1. | Linagliptin | 2.70 |
| 2. | Sorbitol | 50.00 |
| 3. | Lactose | 35.30 |
| | Binder Solution | |
| 4. | Hydroxypropyl methylcellulose | 3.00 |
| 5. | Purified water* | q.s. |
| | Extragranular Ingredients | |
| 6. | Crospovidone | 8.00 |
| 7. | Magnesium stearate | 1.00 |
| | Film Coating | |
| 8. | Opadry ® II yellow | q.s. for 1.5-3.0% |
| 9. | Purified water* | weight build up |

*Lost in Processing
"q.s."—Quantity sufficient

Manufacturing Process:
i) Linagliptin, sorbitol, lactose were sifted and mixed together.
ii) The blend of step (i) was granulated with hydroxypropyl methylcellulose in purified water followed by drying of granules.
iii) The dried granules of step (ii) were blended with crospovidone.
iv) The blend of step (iii) was lubricated with magnesium stearate.
v) Lubricated granules of step (iv) were compressed into tablets using a suitable compression machine.

Coating:
vi) Opadry® II yellow was dispersed in required quantity of purified water under stirring and then stirring was continued for another 45 minutes to form homogeneous dispersion.
vii) Compressed tablets of step (v) were coated with coating dispersion of step (vi) and continued till the target weight build up was achieved.

Example 2

| S. No. | Ingredients | % w/w |
|---|---|---|
| | Intragranular Ingredients | |
| 1. | Linagliptin | 3.50 |
| 2. | Mannitol | 90.00 |
| 3. | Sodium starch glycolate | 2.25 |
| | Binder Solution | |
| 4. | Hydroxypropyl cellulose | 3.25 |
| 5. | Isopropyl alcohol* | q.s. |
| | Extragranular Ingredients | |
| 6. | Magnesium stearate | 1.00 |
| | Film Coating | |
| 7. | Opadry ® II Gray | q.s. for 1.5-2.5% |
| 8. | Purified water* | weight build up |

*Lost in Processing
"q.s."—Quantity sufficient

Manufacturing Process:
The manufacturing process followed is similar to process of preparation provided for example 1.

Examples 3 & 4

| S. No. | Ingredients | Example 3 % w/w | Example 4 % w/w |
|---|---|---|---|
| | Intragranular Ingredients | | |
| 1. | Linagliptin | 2.70 | 2.70 |
| 2. | Microcrystalline cellulose | 67.56 | 91.04 |
| 3. | Dibasic calcium phosphate | 13.53 | — |
| 4. | Maize starch | 10.81 | — |
| | Binder Solution | | |
| 5. | Copovidone | 4.32 | 5.00 |
| 6. | Isopropyl alcohol/ Purified water* | q.s. | q.s. |
| | Extragranular Ingredients | | |
| 7. | Zinc stearate | 1.08 | 1.26 |
| | Film Coating | | |
| 8. | Opadry ® II Pink | q.s. for 1.5-3.0% weight build up | q.s. for 1.5-3.0% weight build up |
| 9. | Purified water* | | |

*Lost in Processing
"q.s."—Quantity sufficient

Manufacturing Process:
The manufacturing process followed is similar to process of preparation provided for example 1.

Example 5

| S. No. | Ingredients | % w/w |
|---|---|---|
| | Intragranular Ingredients | |
| 1. | Linagliptin | 3.5 |
| 2. | Maltodextrin | 88.40 |
| 3. | Hydroxypropyl methylcellulose | 2.70 |
| 4. | Copovidone | 4.32 |
| | Extragranular Ingredients | |
| 5. | Magnesium stearate | 1.08 |
| | Film Coating | |
| 6. | Opadry ® II Blue | q.s. for 1.5-2.7% |
| 7. | Purified water* | weight build up |

*Lost in Processing
"q.s."—Quantity sufficient

Manufacturing Process:
- i) Linagliptin, maltodextrin, hydroxypropyl methyl cellulose, copovidone were sifted and mixed together.
- ii) Magnesium stearate was sifted separately.
- iii) The blend of step (i) was lubricated with magnesium stearate of step (ii) followed by mixing.
- iv) The lubricated granules of step (iii) were compressed into tablets by using suitable compression machine.

Coating:
- v) Coating material was dispersed in required quantity of purified water under stirring and then stirring continued for another 45 minutes to form homogeneous dispersion.
- vi) Compressed tablets of step of (iv) were coated with coating dispersion of step (v) and continued till the target weight build up was achieved.

Example 6

| S. No. | Ingredients | % w/w |
|---|---|---|
| Intragranular Ingredients | | |
| 1. | Linagliptin | 2.70 |
| 2. | Citric acid | 90.00 |
| 3. | Pregelatinised starch | 3.90 |
| 4. | Copovidone | 2.32 |
| Extragranular Ingredients | | |
| 5. | Magnesium stearate | 1.08 |
| Film Coating | | |
| 6. | Opadry ® II Pink | q.s. for 1.5-3.0% weight build up |
| 7. | Purified water* | |

*Lost in Processing
"q.s."—Quantity sufficient

Manufacturing Process:

The manufacturing process followed is similar to process of preparation provided for example 5.

Examples 7, 8, 9 & 10

| S. No. | Strategy | Example 7 % w/w | Example 8 % w/w | Example 9 % w/w | Example 10 % w/w |
|---|---|---|---|---|---|
| Ingredients | | | | | |
| 1. | Linagliptin | 2.703 | 2.703 | 2.703 | 2.703 |
| 2. | Mannitol | — | 20.432 | — | — |
| 3. | Microcrystalline cellulose | 88.582 | 68.324 | — | — |
| 4. | Sorbitol | — | — | 91.341 | — |
| 5. | Xylitol | — | — | — | 91.341 |
| 6. | Corn starch | 1.039 | 0.973 | 1.000 | 1.000 |
| 7. | Copovidone | 1.946 | 2.919 | 0.751 | 0.751 |
| 8. | Pregelatinized starch | 1.946 | 0.973 | — | — |
| 9. | Magnesium stearate | 1.081 | 0.973 | 1.503 | 1.503 |
| Film Coating | | | | | |
| 10. | Opadry ® II Gray | q.s. for 1.5-3.0% weight build up | | | |
| 11. | Purified water* | | | | |

*Lost in Processing
"q.s."—Quantity sufficient

Manufacturing Process:

The manufacturing process followed for examples 7, 8 and 10 is similar to process of preparation provided for example 1.

The manufacturing process followed for example 9 is similar to process of preparation provided for example 5.

Examples 11 & 12

| S. No. | Ingredients | Example 11 % w/w | Example 12 % w/w |
|---|---|---|---|
| Intragranular Ingredients | | | |
| 1. | Linagliptin | 2.70 | 2.70 |
| 2. | Xylitol | — | 90.25 |
| 3. | Mannitol | 89.0-93.0 | — |
| 4. | Pregelatinised starch | 1.80-2.00 | — |
| 5. | Croscarmellose sodium | 1.00-3.00 | — |
| 6. | Sodium starch glycolate | — | 4.0 |
| Binder Solution | | | |
| 7. | Copovidone | 0.5-2.0 | 2.05 |
| 8. | Purified water* | q.s. | — |
| 9. | Isopropyl alcohol* | — | q.s. |
| Extragranular Ingredients | | | |
| 10. | Magnesium stearate | 0.80-1.50 | — |
| 11. | Zinc stearate | — | 1.00 |
| Film Coating | | | |
| 12. | Opadry ® II Yellow | q.s. for 1.5-3.0% weight build up | |
| 13. | Purified water* | | |

*Lost in Processing
"q.s."—Quantity sufficient

Manufacturing Process:

The manufacturing process followed is similar to process of preparation provided for example 1.

Example 13

| S. No | Ingredients | % w/w |
|---|---|---|
| Intragranular Ingredients | | |
| 1. | Linagliptin | 2.70 |
| 2. | Metformin hydrochloride | 50.00 |
| 3. | Dibasic calcium phosphate | 32.80 |
| 4. | Pregelatinized starch | 10.50 |
| Binder Solution | | |
| 5. | Hydroxypropyl methylcellulose | 3.00 |
| 6. | Purified water* | q.s. |
| Extagranular Ingredients | | |
| 7. | Magnesium stearate | 1.00 |

*Lost in Processing
"q.s."—Quantity sufficient

Manufacturing Process:
- i) Linagliptin, metformin hydrochloride, dibasic calcium phosphate and pregelatinised starch were sifted and mixed together.
- ii) The blend of step (i) was granulated with hydroxypropyl methylcellulose in purified water followed by drying of granules.
- iii) The dried granules of step (ii) were lubricated with magnesium stearate.
- iv) Lubricated granules of step (iii) were compressed into tablets using a suitable compression machine.

Example 14

| S. No. | Strategy | % w/w |
|---|---|---|
| | Ingredients | |
| 1. | Linagliptin | 2.71 |
| 2. | Mannitol | 89.70 |
| 3. | Microcrystalline cellulose | — |
| 4. | Sorbitol | — |
| 5. | Xylitol | — |
| 6. | Corn starch | 1.00 |
| 7. | Copovidone | 2.71 |
| 8. | Pregelatinized starch | — |
| 9. | Magnesium stearate | 1.49 |
| | Film Coating | |
| 10. | Opadry ® 03F540136 Pink | q.s. for 1.5- |
| 11. | Purified water* | 3.5% weight build up |

*Lost in Processing
"q.s."—Quantity sufficient

Manufacturing Process:

i) Linagliptin, Mannitol and Corn starch were co-sifted and mixed together.

ii) The blend of step (i) was granulated with Copovidone in purified water followed by drying of granules.

iii) The dried granules of step (ii) were lubricated with Magnesium stearate.

iv) Lubricated granules of step (iii) were compressed into tablets using a suitable compression machine.

v) The compressed tablets of step (iv) were film-coated.

Examples 15, 16 & 17

| S. No. | Strategy | Example 15 % w/w | Example 16 % w/w | Example 17 % w/w |
|---|---|---|---|---|
| | Ingredients | | | |
| 1. | Linagliptin | 2.703 | 2.703 | 2.703 |
| 2. | Mannitol | — | — | — |
| 3. | Microcrystalline cellulose | 90.528 | — | — |
| 4. | Sorbitol | — | — | 91.341 |
| 5. | Xylitol | — | 91.341 | — |
| 6. | Corn starch | 1.039 | 1.000 | 1.000 |
| 7. | Copovidone | 1.946 | 0.751 | 0.751 |
| 8. | Pregelatinized starch | — | — | — |
| 9. | Magnesium stearate | 1.081 | 1.503 | 1.503 |
| | Film Coating | | | |
| 10. | Opadry ® II Purple | q.s. for 1.5-3.0% weight build up | | |
| 11. | Purified water* | | | |

*Lost in Processing
"q.s."—Quantity sufficient

Manufacturing Process:

The manufacturing process followed for examples 15 and 16 is similar to process of preparation provided for example 1.

The manufacturing process followed for example 17 is similar to process of preparation provided for example 5.

Examples 18, 19 & 20

| S. No. | Strategy | Example 18 % w/w | Example 19 % w/w | Example 20 % w/w |
|---|---|---|---|---|
| | Ingredients | | | |
| 1. | Linagliptin | 2.778 | 2.778 | 2.788 |
| 2. | Mannitol | 84.004 | 81.003 | 88.005 |
| 3. | Corn starch | 8.911 | 11.912 | 4.910 |
| 4. | Copovidone | 2.778 | 2.778 | 2.778 |
| 5. | Magnesium stearate | 1.530 | 1.530 | 1.530 |
| | Film Coating | | | |
| 6. | Opadry ® 03F540136 Pink | q.s. for 1.5-3.5% weight build up | q.s. for 1.5-3.5% weigh build up | q.s. for 1.5-3.5% weight build up |
| 7. | Purified water* | | | |

*Lost in Processing
"q.s."—Quantity sufficient

Manufacturing Process:

The manufacturing process followed for examples 18, 19 & 20 is similar to process of preparation provided for example 14.

Reference Example 1

| S. No. | Strategy | % w/w |
|---|---|---|
| | Ingredients | |
| 1. | Linagliptin | 2.778 |
| 2. | Mannitol | 92.914 |
| 3. | Copovidone | 2.778 |
| 4. | Magnesium stearate | 1.530 |
| | Film Coating | |
| 5. | Opadry ® 03F540136 Pink | q.s. for 1.5- |
| 6. | Purified water* | 3.5% weight build up |

*Lost in Processing
"q.s."—Quantity sufficient

Manufacturing Process:

The manufacturing process followed for reference examples 1 is similar to process of preparation provided for prepared according to invention covered under U.S. Pat. No. 9,867,829.

Tablets of example 18 and reference example 1 were subject to stability study at 40° C./75% RH for 15 days in open petri dish. The dissolution of tablets was determined in a basket apparatus containing 6 identical vessels and stirring apparatus to allow simultaneous analysis of six tablets. The measurements were made at 37±0.5° C. with a basket speed of 50 rpm in 900 ml 0.1 N HCl as dissolution medium. At every regular time interval, a sample was taken from each of the vessels. The sample was taken from the zone midway between the surface of the dissolution medium and the top of the basket, not less than 1 cm from the vessel wall. The sample was injected into a UV analyzer to determine the amount of the dissolved active ingredient linagliptin. The amount of the detected linagliptin in percent (%) based on the original amount of the linagliptin present in the tablet used for the dissolution test measured is given in the below table.

Percentage of dissolution (%)

| Time (min) | Example 18 | | Reference Example 1 | |
|---|---|---|---|---|
| | Initial | Stability Study | Initial | Stability Study |
| 5 | 85 | 29 | 38 | 25 |
| 10 | 102 | 89 | 52 | 39 |
| 15 | 102 | 104 | 60 | 52 |
| 20 | 102 | 104 | 71 | 64 |
| 30 | 102 | 105 | 96 | 83 |
| 45 | 102 | 104 | 100 | 99 |

It can be concluded from the above table that the composition according to Reference Example 1 (where mannitol is more than 90%) shows very slow dissolution rate, especially up to 30 minutes in both the condition i.e. initial and stability study (40° C./75% RH for 15 days in open petri dish). Whereas, composition according to Example 18 (where mannitol is 84%) shows no significant effect on dissolution rate in both the condition i.e. initial and stability study (40° C./75% RH for 15 days in open petri dish).

The rate of dissolution is very slow in the composition (Reference example 1) which has higher amount of mannitol (more than 90%). This means composition with high amount of mannitol does not provide appropriate release of drug (Linagliptin) which in turn will affect the dissolution rate and in turn bioequivalence.

We claim:

1. A single layered coated tablet composition consisting of linagliptin in an amount of 2 to 3% w/w, mannitol in an amount of 80 to 90% w/w, copovidone in an amount of 2 to 3% w/w, corn starch in an amount of 0.5 to 10% w/w, and magnesium stearate in an amount of 1 to 2% w/w, wherein said % w/w is based upon total weight of tablet, with the proviso that the tablet composition is free of pregelatinised starch and the said coating consisting of hydroxypropyl methyl cellulose, and wherein at least 85% of linagliptin in the tablet is dissolved in 10 minutes when tablet stored for at least 2 weeks at about 40° C./75% RH.

* * * * *